(12) United States Patent
Colosio

(10) Patent No.: US 10,099,021 B2
(45) Date of Patent: Oct. 16, 2018

(54) INHALER DEVICE

(71) Applicant: CMS DI COLOSIO MAURO, Brescia (IT)

(72) Inventor: Mauro Colosio, Brescia (IT)

(73) Assignee: CMS DI COLOSIO MAURO, Brescia (IT)

(*) Notice: Subject to any disclaimer, the term of this patent is extended or adjusted under 35 U.S.C. 154(b) by 801 days.

(21) Appl. No.: 14/432,599

(22) PCT Filed: Oct. 2, 2012

(86) PCT No.: PCT/IT2012/000302
§ 371 (c)(1),
(2) Date: Mar. 31, 2015

(87) PCT Pub. No.: WO2014/054059
PCT Pub. Date: Apr. 10, 2014

(65) Prior Publication Data
US 2015/0283338 A1  Oct. 8, 2015

(51) Int. Cl.
*A61M 16/00* (2006.01)
*A61M 15/00* (2006.01)
*A61M 11/00* (2006.01)

(52) U.S. Cl.
CPC .... *A61M 15/0031* (2014.02); *A61M 15/0021* (2014.02); *A61M 15/0028* (2013.01); *A61M 15/0043* (2014.02); *A61M 11/003* (2014.02); *A61M 2202/0007* (2013.01); *A61M 2202/064* (2013.01)

(58) Field of Classification Search
CPC ............ A61M 15/0028; A61M 15/003; A61M 15/0043; A61M 15/0031; A61J 3/07; A61J 7/0007

USPC ..................................................... 128/203.15
See application file for complete search history.

(56) References Cited

U.S. PATENT DOCUMENTS

| | | | | |
|---|---|---|---|---|
| 3,518,992 A * | 7/1970 | Howell | ............. | A61M 15/0028 128/203.15 |
| 4,210,140 A * | 7/1980 | James | ................ | A61M 15/0028 604/58 |
| 4,446,862 A * | 5/1984 | Baum | ................ | A61M 15/0028 128/203.15 |
| 5,522,383 A * | 6/1996 | Calvert | ............. | A61M 15/0028 128/203.15 |

(Continued)

FOREIGN PATENT DOCUMENTS

| EP | 0028162 | 5/1981 |
|---|---|---|
| EP | 0028162 A1 | 5/1981 |

(Continued)

OTHER PUBLICATIONS

International Search Report dated Jul. 2, 2013.

*Primary Examiner* — Kari Rodriquez
*Assistant Examiner* — Victoria Murphy
(74) *Attorney, Agent, or Firm* — Thomas Horstemeyer, LLP

(57) ABSTRACT

An inhaler device of a powdered substance contained in a capsule comprises a capsule seat suitable for receiving the capsule, said capsule seat being made in two parts which can be reciprocally distanced, each capsule seat part being suitable for retaining a respective capsule part. Means of separation are operable to cause the distancing of said two capsule seat parts.

17 Claims, 8 Drawing Sheets

(56) References Cited

U.S. PATENT DOCUMENTS

| | | | | |
|---|---|---|---|---|
| 5,819,730 | A * | 10/1998 | Stone | A61M 15/0028 128/200.14 |
| 5,896,855 | A * | 4/1999 | Hobbs | A61M 15/0028 128/203.12 |
| 6,089,228 | A * | 7/2000 | Smith | A61M 15/0045 128/203.15 |
| 6,470,884 | B2 * | 10/2002 | Horlin | A61M 15/0028 128/203.15 |
| 6,679,255 | B2 * | 1/2004 | Pera | A61M 15/0028 128/203.12 |
| 7,143,765 | B2 * | 12/2006 | Asking | A61M 15/0045 128/203.15 |
| 8,584,669 | B2 * | 11/2013 | Besseler | A61M 15/0028 128/200.11 |
| 9,415,177 | B2 * | 8/2016 | Baillet | A61M 15/0028 |
| 2003/0150297 | A1 * | 8/2003 | Mazur | A61J 7/0007 81/3.09 |
| 2004/0043064 | A1 * | 3/2004 | Iorio | A61K 9/4891 424/452 |
| 2004/0236282 | A1 * | 11/2004 | Braithwaite | A61M 15/0045 604/158 |
| 2005/0238708 | A1 * | 10/2005 | Jones | A61K 9/4808 424/451 |
| 2005/0268909 | A1 * | 12/2005 | Bonney | A61M 15/0028 128/203.15 |
| 2013/0047985 | A1 * | 2/2013 | Harris | A61M 15/0028 128/203.15 |
| 2013/0152927 | A1 * | 6/2013 | Baillet | A61M 15/0028 128/203.15 |
| 2015/0283338 | A1 * | 10/2015 | Colosio | A61M 15/0028 128/203.15 |

FOREIGN PATENT DOCUMENTS

| | | |
|---|---|---|
| EP | 0581473 | 2/1994 |
| EP | 0581473 A1 | 2/1994 |
| EP | 1270034 | 1/2003 |
| EP | 1270034 A2 | 1/2003 |
| JP | 2006280676 | 10/2006 |
| JP | 2006280676 A | 10/2006 |
| WO | 8201470 | 5/1982 |
| WO | 8201470 A1 | 5/1982 |
| WO | 2012004512 | 1/2012 |
| WO | 2012004512 A1 | 1/2012 |

* cited by examiner

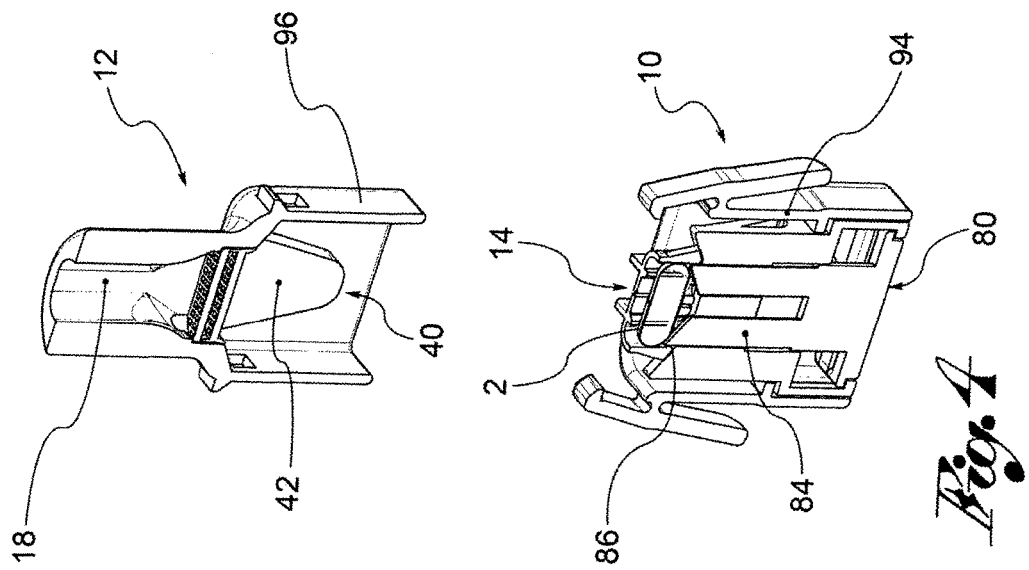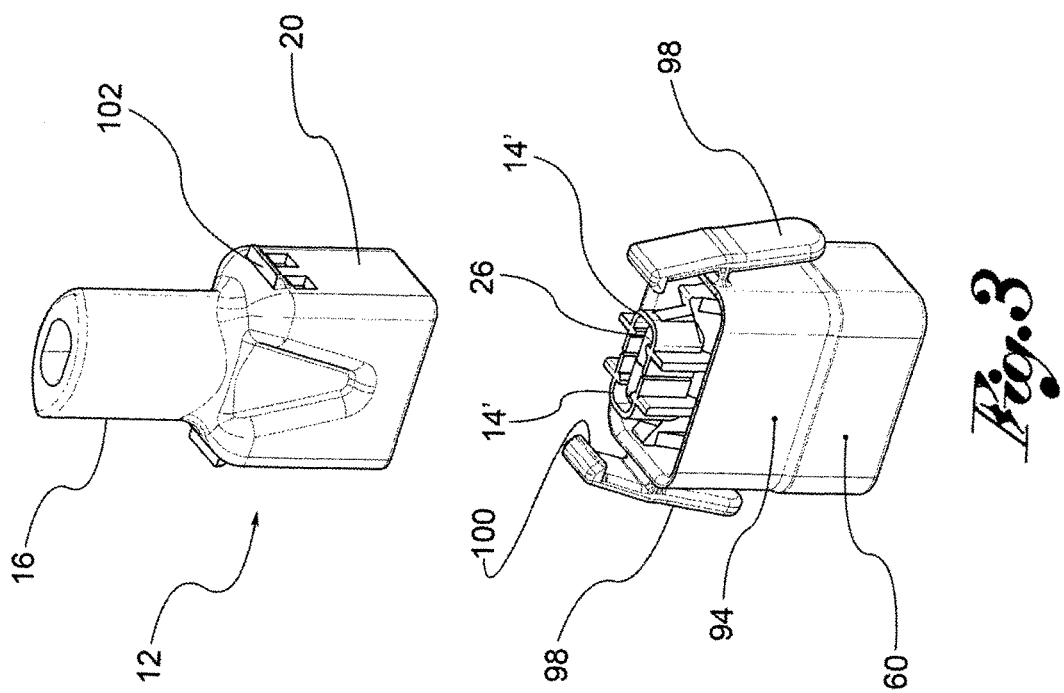

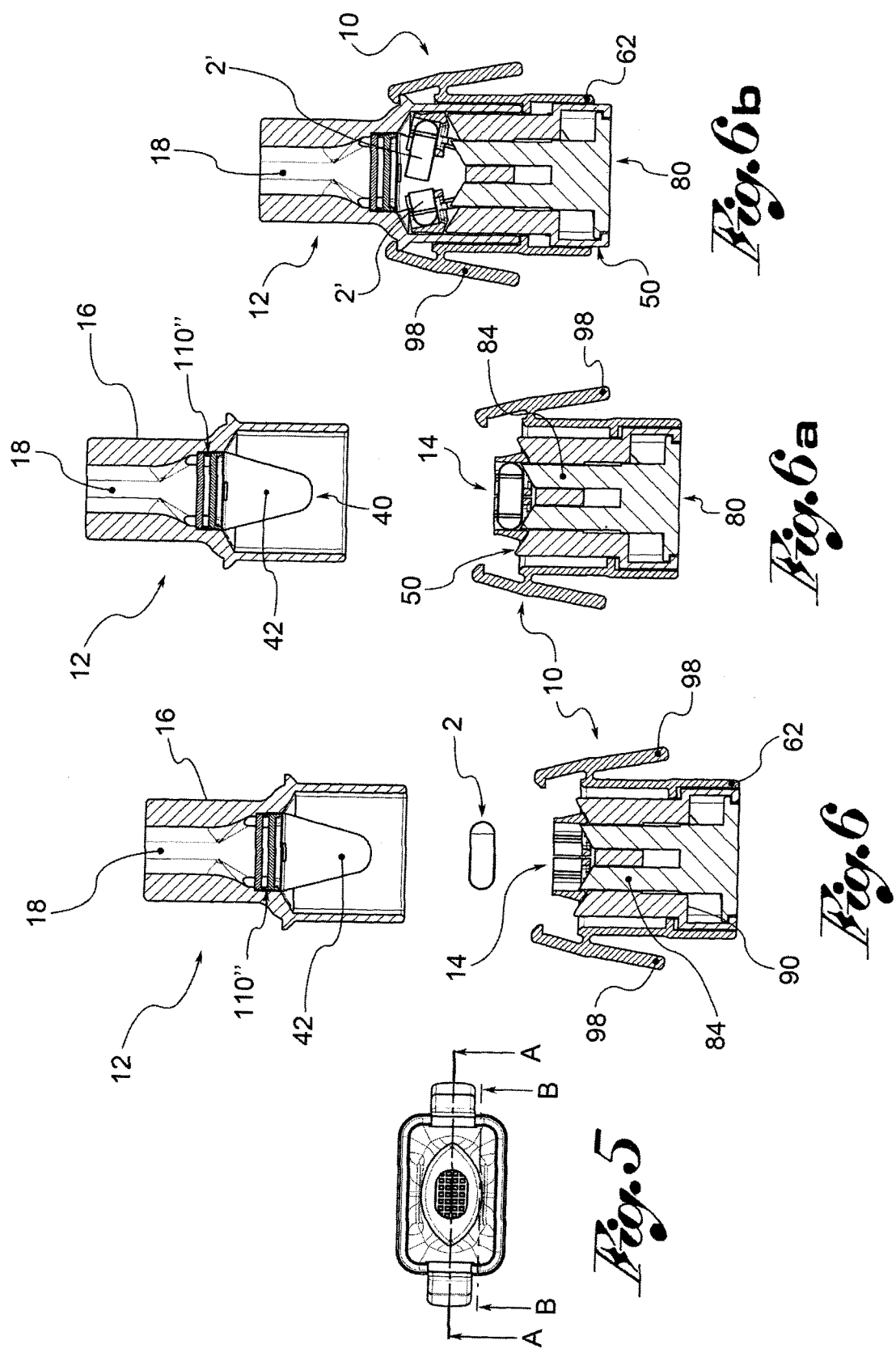

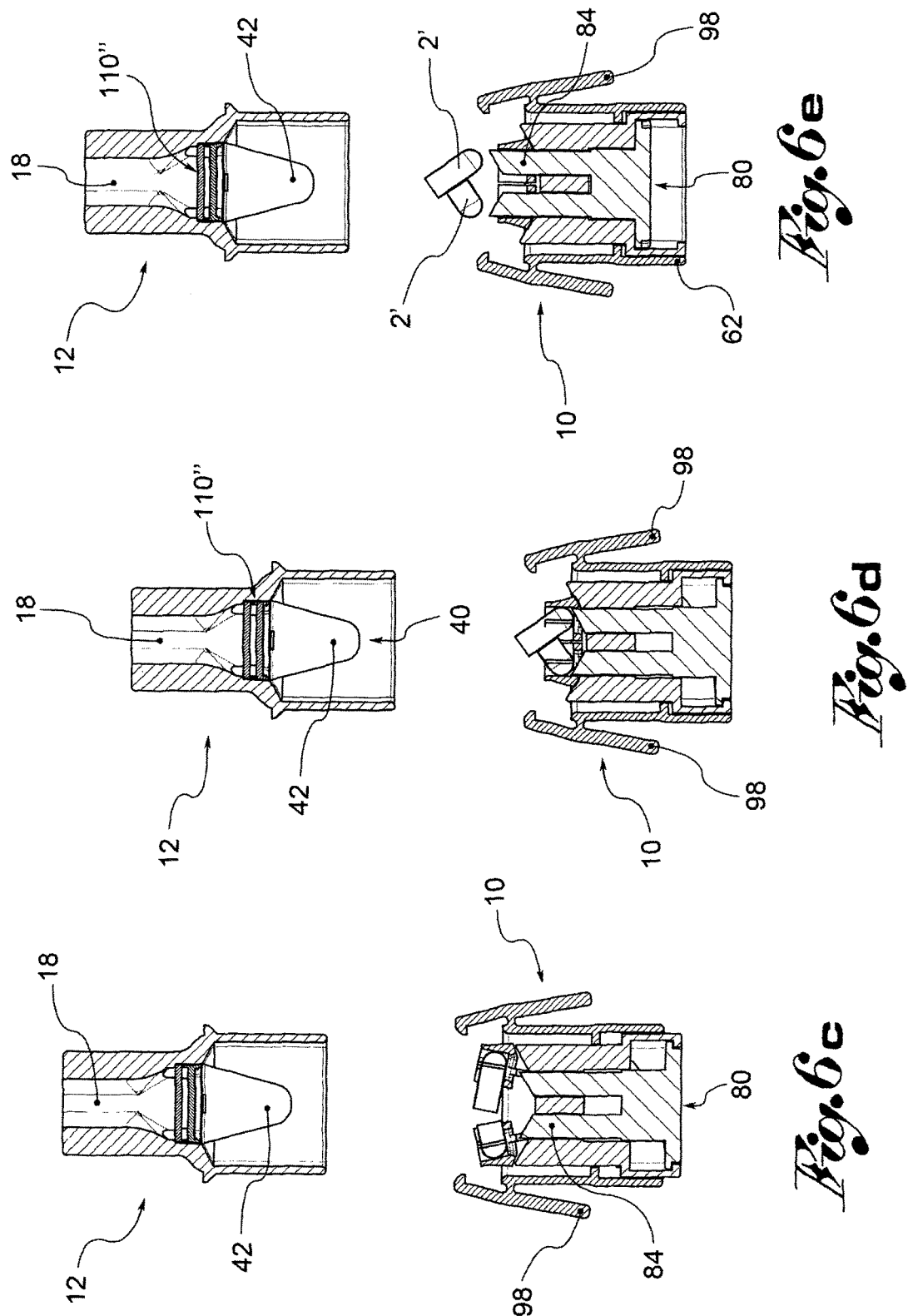

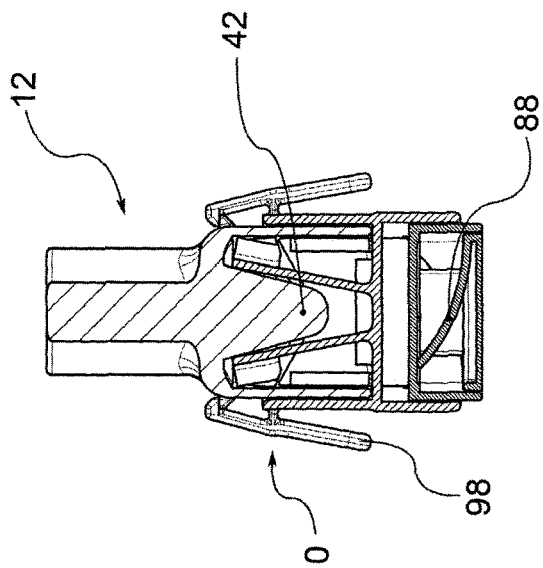
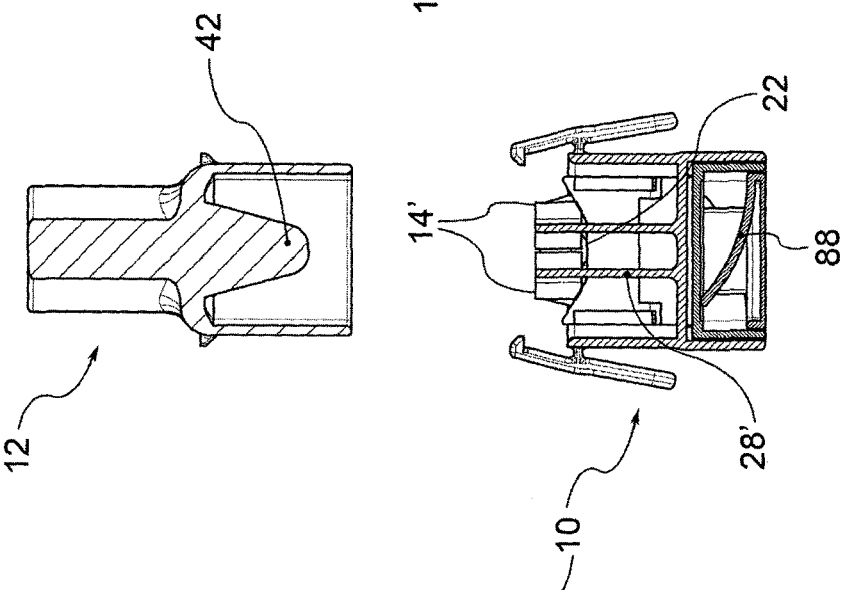
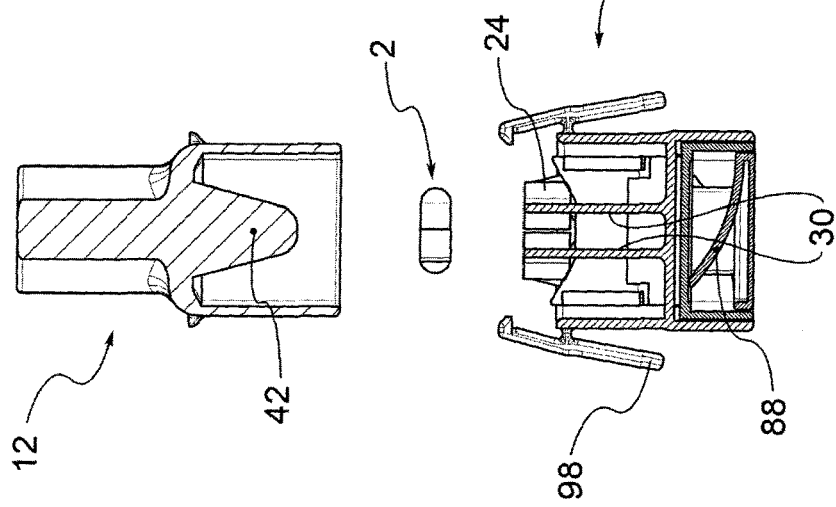

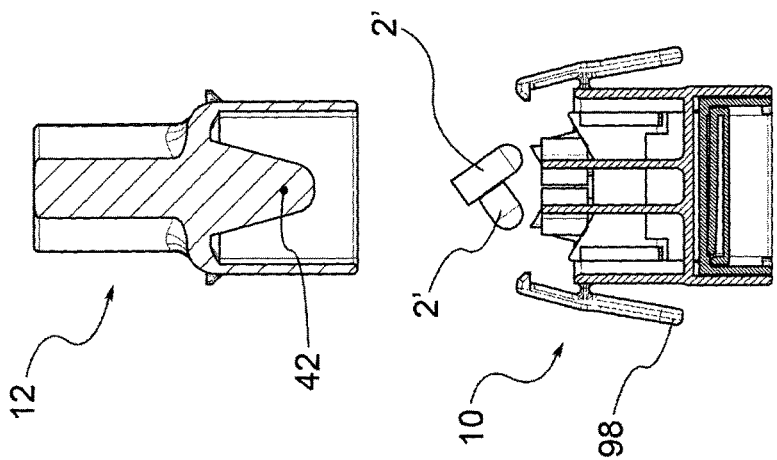
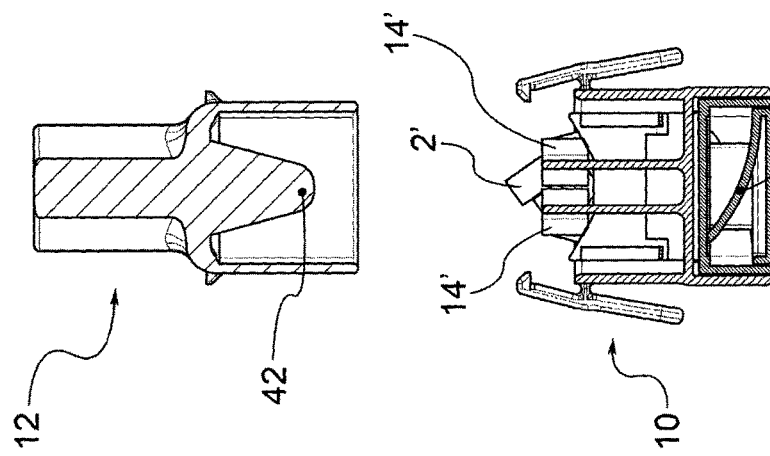
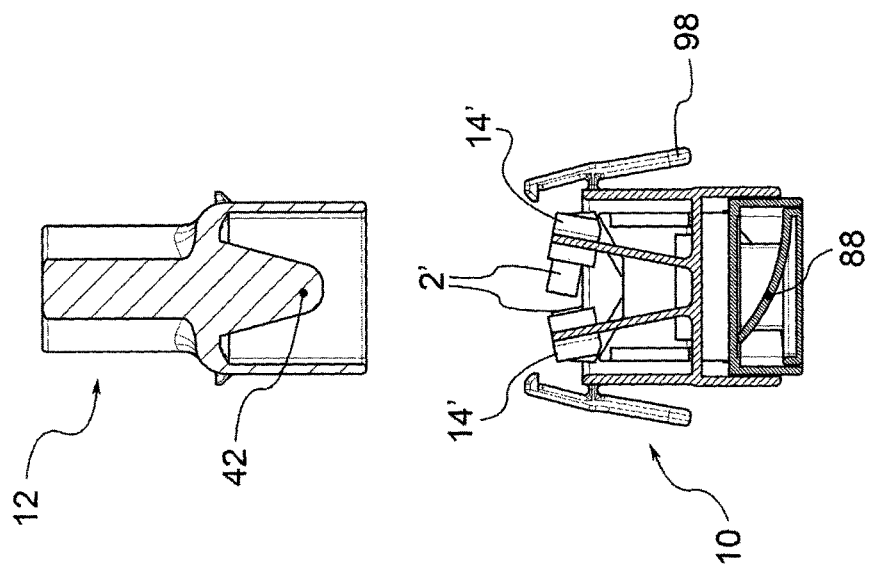

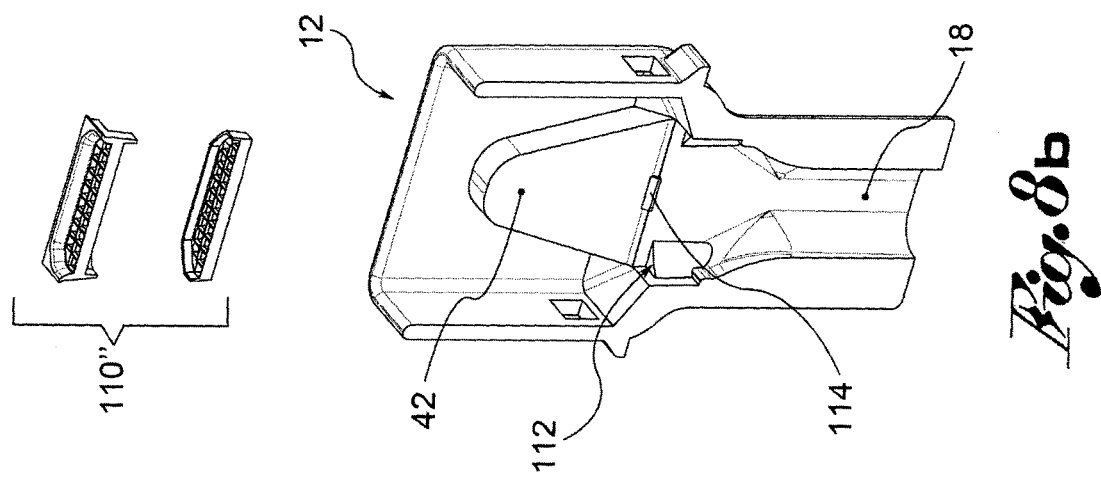
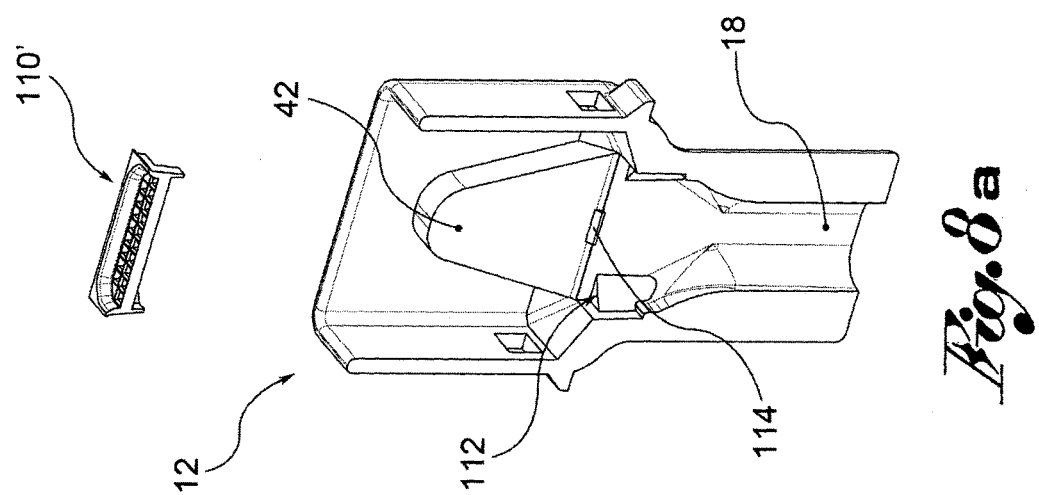
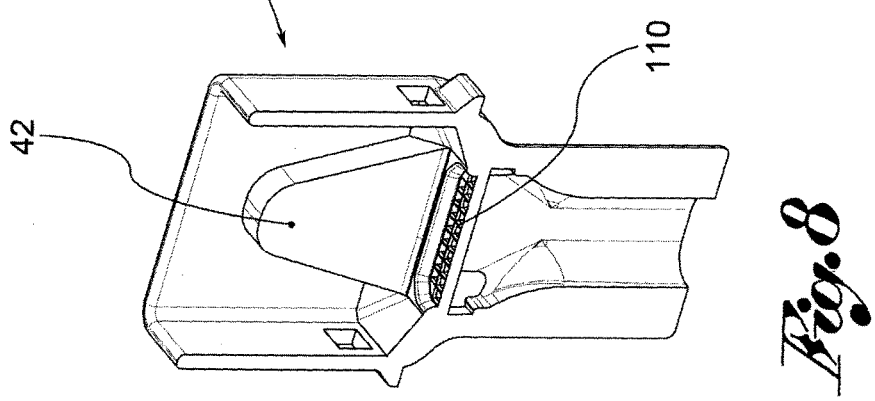

INHALER DEVICE

CROSS-REFERENCE TO RELATED APPLICATION

This application is the 35 U.S.C. § 371 national stage application of PCT Application No. PCT/IT2012/000302, filed Sep. 2, 2012, the entirety of which is hereby incorporated by reference.

The present invention relates to an inhaler device suitable for releasing into the airways of a patient a powdered substance dosed and contained in a capsule having a closed container, also called operculum, formed of two separable parts. For example, said capsule may be any colour, format or size according to pharmaceutical classification from 2 to 3, preferably 3.

The product contained in the capsule consists in fact of a single chemical unit or several chemical units, of which one or more may be pharmaceutical active substances with recognised pharmaceutical activity or excipients. In particular, the formulation of the substance contained in the capsule consists of both micronised material (active or excipient) and non micronised material (preferably excipient only). Micronised is taken to mean a product with average aerodynamic dimensions of less than 20 micron (preferably 0 to 5 micron); non-micronised is taken to mean a product over 20 micron, preferably 20 to 200 micron.

Inhaler devices of this type are already known of, comprising a mouthpiece and a body which a seat is made in suitable for receiving a capsule containing the powdered substance to inhale. Means of aperture of the capsule, operable by the user or automatic, required for the purpose of permitting the passage through the capsule or operculum of a flow of air coming from the outside which, mixing with the powdered substance, enables the latter to be extracted from the operculum and redirected towards the mouthpiece of the device and thus towards the user-patient, are associated to said body.

Usually, said means of aperture envisage the perforation of one or more parts of said capsule. Such devices generally comprise a pair of needles or cylinders or perforating devices which are introduced into the intact capsule at the moment of, or immediately prior to, preparation of the dose to be assimilated. Such perforation devices which cause the perforation of the intact walls of the capsule are a common working mechanism needed to extract the dose from the operculum to the patient. One example of such inhaler devices is described in EP1270034A2.

One possible drawback of the prior inhaler devices is that the perforation of the capsule causes the formation of fragments of the operculum which may be mixed with the powdered substance and which may therefore be inhaled by the patient.

Another drawback of such devices is that the formation of small holes in the capsule does not ensure that all the powdered substance is inhaled. Very often a certain undefined quantity of substance remains in the capsule which is not extracted and which is therefore not used or which is used accidentally during subsequent applications.

In addition, the known inhaler devices are necessarily composed of a large number of parts given the need to provide a device for the perforation of the capsule, for example parts in plastic and parts in metal, such as needles and springs, needed to activate the opening mechanism, which make both the production and the assembly of the device expensive, considerably influencing the final cost of the product.

Devices with a large number of components have a greater combination of malfunction risk factors and may therefore have an intrinsically greater risk of defectiveness in that they require greater care in the assembly of the single components.

The purpose of the present invention is to propose an inhaler device able to overcome the drawbacks complained of above, in particular reducing the production cost, maintaining or improving performance and the consistency of the dose emitted.

Such purpose is achieved by an inhaler device according to claim 1.

According to one aspect of the invention, the inhaler device comprises a capsule seat suitable for receiving the capsule, said capsule seat being made in two parts which can be reciprocally distanced. The two capsule seat parts are suitable for retaining the operculum of the capsule, a portion of the capsule in each corresponding part of the capsule seat.

The device comprises means of separation operable to cause the distancing of said two capsule seat parts.

Preferably, each of the two capsule seat parts is suitable for blocking the capsule by interference with the walls of the operculum of the capsule.

In particular, each of the two capsule seat parts is suitable to interfere with the walls of the operculum of the capsule without causing the perforation or abrasion of said walls.

According to another aspect of the invention, the inhaler device comprises capsule seat blocking means movable from an active position, in which they block the two parts of capsule seat in a capsule insertion position, to an inactive position, in which they permit the distancing of said two capsule seat parts. This way, the capsule is insertable in the respective seat in a rapid and secure manner.

According to another aspect of the invention, the inhaler device comprises in addition capsule extractor means, operable, after use, to penetrate the two capsule seat parts so as to expel the two separated capsule parts.

The dependent claims describe preferred or advantageous embodiments of the inhaler device.

The characteristics and advantages of the inhaler device according to the invention will, in any case, be evident from the description given below of its preferred embodiments, made by way of a non-limiting example with reference to the appended drawings, wherein:

FIG. 3 is a perspective view of the inhaler device and the mouthpiece, separated from each other;

FIG. 4 is a perspective view and in axial cross-section of the inhaler device and the mouthpiece, separated from each other;

FIG. 5 is a ground view from above of the inhaler device;

FIGS. 6-6e are views of the inhaler device in cross-section along the line A-A in FIG. 5, in the same number of functioning steps of the device;

FIGS. 7-7e are views of the inhaler device in cross-section along the line B-B in FIG. 5, in the same number of functioning steps of the device; and FIGS. 8-8b are perspective views in axial cross-section of the same number of embodiments of the mouthpiece.

Figure 1:
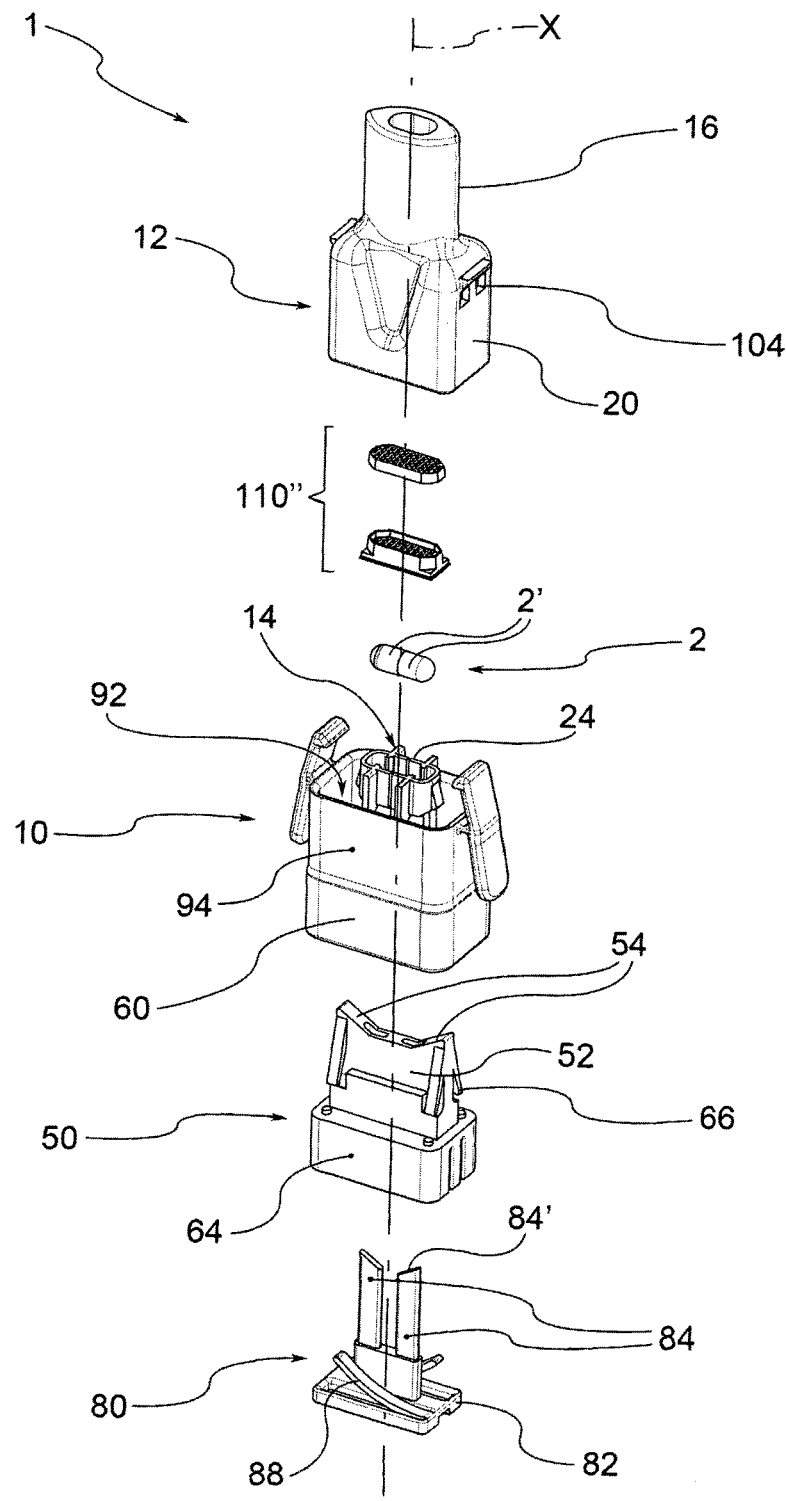
FIG. 1 is an exploded perspective view of the inhaler device according to the invention.
Figure 2:
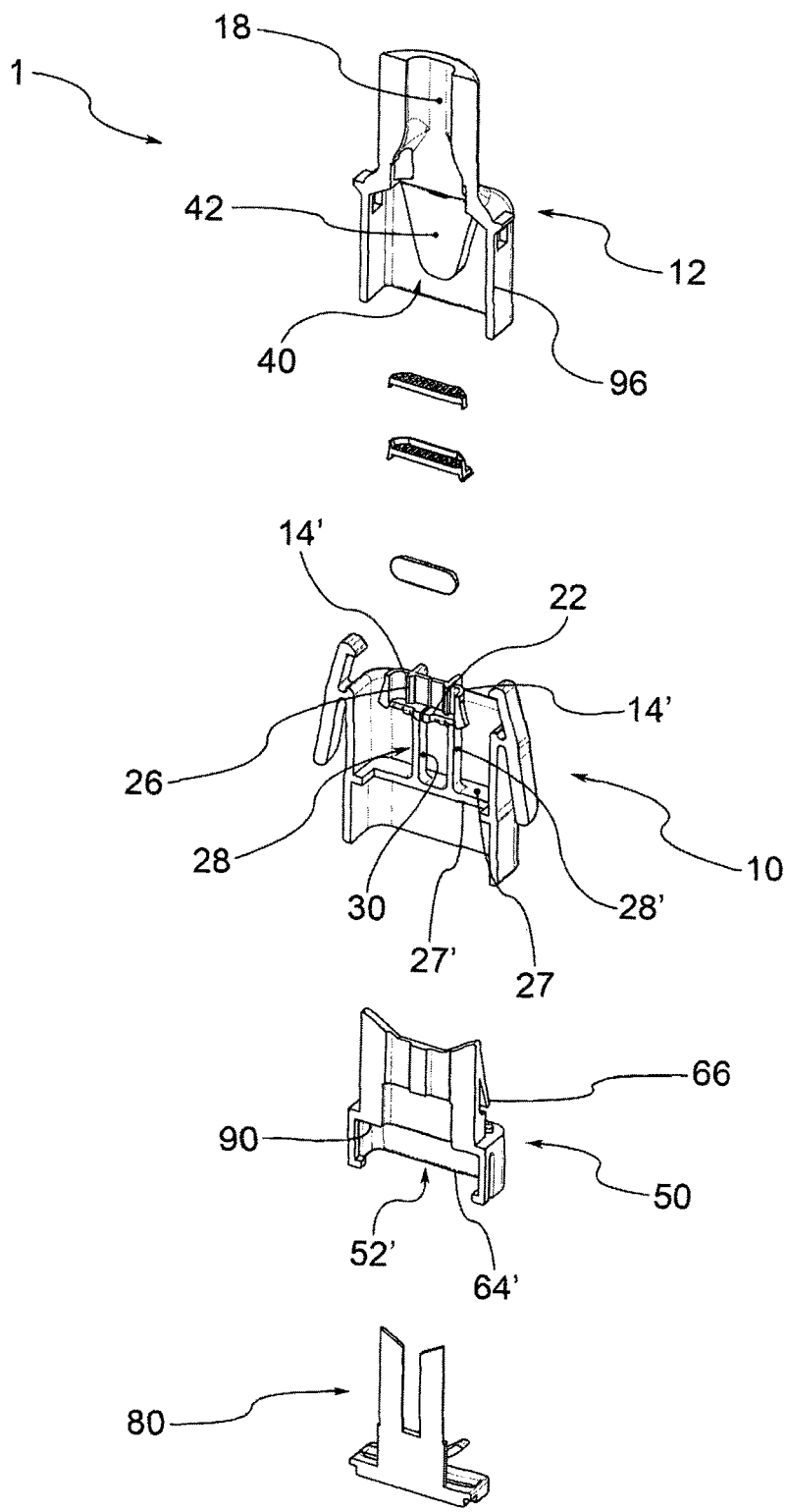
FIG. 2 is an exploded perspective and axially cross-sectioned view of the inhaler device according to the invention.

In said drawings, reference numeral 1 globally denotes an inhaler device of at least one powdered substance contained in a capsule 2 of the type having an operculum formed of two parts.

The inhaler device 1 comprises an inhaler body 10 and a mouthpiece 12 coupling in a detachable manner to the inhaler body 10. A capsule seat 14 suitable for receiving the capsule 2 is made in the inhaler body 10. The mouthpiece 12 has an upper portion 16 defining an exit passage in fluidic communication with said capsule seat 14, and a base 20 coupling to the inhaler body 10.

The inhaler device 1 extends mainly along a main axis X. In the continuation of the description, reference will be made, for simplicity of exposition, to the inhaler device 1 positioned on a support surface, this also being the position in which the capsule 2 is inserted in the capsule seat 14, as described further below. In such condition, the main axis X may be considered vertical.

In a preferred embodiment, the capsule seat 14 is in the form of a tray orientated horizontally. In other words, the capsule seat 14 has a horizontal end wall 22, facing downwards, and a lateral rim 24, preferably vertical. The capsule seat 14 is therefore open at the top to receive the capsule 2 from above. In a preferred embodiment, the capsule seat 14 is shaped in a complementary manner to the capsule 2.

Consequently, the capsule seat 14 is a rectangular shape, with the short sides rounded, in a corresponding manner to the spherical ends of the capsule 2.

According to one aspect of the invention, the capsule set 14 is formed of two parts 14' separate from each other and which can be reciprocally distanced, each capsule seat part 14' being suitable to retain a respective capsule part 2'. In other words, the two parts 14' of the capsule seat 14 are movable from an initial position, in which they are alongside each other or in any case facing so as to receive a whole capsule 2, and a final position, in which they are distanced from each other so as to cause the separation of the two parts 2' of the capsule 2 and thereby permit the mixing of a flow of air coming from outside with the powdered substance contained in the capsule 2.

As will be described in more detail below, the inhaler device 1 is provided with means of separation 40 operable to cause the distancing of said parts 14' of the capsule seat 14.

In a preferred embodiment, the two parts 14' of capsule seat 14 are suitable for retaining by calibrated interference the respective parts 2' of capsule 2. In other words, the intact capsule 2 is pressure inserted, that is exerting a slight force, in the capsule seat 14. Calibrated interference is taken to mean, moreover, that the interference between the capsule seat 14 and the walls of the operculum of the capsule 2 is such as not to cause the perforation of said walls.

For example, from the lateral rim 24 of each of the two parts 14' of capsule seat 14 two gripping teeth 26 extend inwards suitable for incising and/or deforming the walls of the operculum of the capsule 2 without causing the perforation or fragmentation thereof.

In a preferred embodiment, the two parts 14' of capsule seat 14 are separated along a vertical plane and preferably perpendicular to the longer sides of the capsule seat 14.

In one embodiment, the inhaler body 10 has an end wall 27 from which a pair of elastic arms 28 extends vertically. Each of the two parts 14' of capsule seat 14 is attached to the top of a respective elastic arm 28.

As will be described in more detail below, the reciprocal distancing of the two parts 14' of capsule 14 is achieved thanks to the flexing of each elastic arm 28 in relation to its lower end attached to the end wall 27 of the inhaler body, that is, thanks to the divarication of the two flexible arms 28.

To such purpose, the elastic arms 28 have respective divarication surfaces 30 parallel and facing each other, which the separation means 40 described below act on.

It is to be noted that when divarication has been performed by the separation means 40, the two parts 14' of capsule seat 14 are inclined with the relative ends facing each other upwards. Consequently, during and at the end of the opening step of the capsule 14, all the powdered substance remains in the two capsule parts 14' and does not fall downwards.

In a preferred embodiment, each elastic arm 28 is formed of two parallel rods 28' the upper ends of which are attached to opposite sides of the lateral rim 24 of a respective part 14' of capsule seat 14. This way, the space below the end wall 22 of the capsule seat 14 is left free. Preferably, seen in transversal cross-section, such parallel rods 28' extend mainly in a direction orthogonal to the distancing direction of the two parts 14' of capsule 14, so that the rods attached to the same longer side of the capsule seat 14 form the divarication surfaces 30 parallel and facing each other.

In order to cause the divarication of the elastic arms 28, the separation means 40 comprise at least one wedge-shaped element 42 associated to the mouthpiece 12 and suitable for inserting itself between said divarication surfaces 30 when the mouthpiece 12 is fitted to the inhaler body 10.

According to another aspect of the invention, the inhaler device 1 comprises capsule seat blocking means 50 movable from an active position, in which they block the two parts 14' of capsule seat 14 in a capsule insertion position, to an inactive position, in which they permit the distancing of said two parts 14' of capsule seat 14. Consequently, the insertion of the capsule 2 in the relative capsule seat 14 is facilitated by the fact that the two parts 14' of the capsule seat do not move when the user performs such pressure insertion. Given that the capsule seat 14 is counter shaped in relation to the capsule 2, the absence of movement and therefore of clearance permits a univocal position of the capsule in the relative seat to be defined.

For example, the capsule 2 may be placed in a horizontal position on the lateral rim 24 and on the gripping teeth 26 of the capsule seat and then simply pressed downwards. The blockage of the two parts 14' of the capsule seat 14 prevents the two parts from opening during such pressure.

In a preferred embodiment, said capsule seat blocking means 50 comprise a blocking tooth 52 which extends into the inhaler body 10, for example under the capsule seat 14 thanks to the conformation of the elastic arms 28 described above. The blocking tooth 52 ends at the top with support surfaces 54, each suitable for engaging a respective part 14' of the capsule seat 14. The blocking tooth 52 is movable between a lowered position, in which said support surfaces 54 do not interfere with the distancing movement of the two parts 14' of capsule seat 14, and a raised position, wherein said support surfaces 54 press said parts 14' of capsule seat 14 against each other.

Preferably, each of said support surfaces 54 is formed of an inclined plane with decreasing incline towards the capsule seat 14. In particular, when the blocking tooth 52 translates in a vertical direction upwards, each inclined plane engages a respective end of the capsule seat 14 with a component force directed horizontally towards the opposite end.

According to one embodiment, the inhaler body 10 has a hollow lower portion 60 which extends under the end wall 27 of the inhaler body 10 and which terminates with a lower rim 62 defining a support base of a support surface.

The blocking tooth 52 has a lower actuation portion 64 which extends in said lower hollow portion 60 passing through an aperture 27' made in the end wall 27 of the inhaler body 10.

In a preferred embodiment, when the blocking tooth 52 is in an inactive lowered position, said lower actuation portion 64 projects downwards from said lower rim 62. When, instead, the blocking tooth 52 is in a raised blocking position of the capsule seat 14, said lower actuation portion 64 is aligned with said lower rim 62.

Such execution facilitates the use of the inhaler device 1, and in particular the insertion of the capsule 2 in the relative seat 14. In fact, to block the capsule seat 14 in the initial capsule insertion position, it is sufficient to place the inhaler body on a surface, so that the blocking tooth 52 raises itself until its lower actuation portion 64 is aligned with the lower rim 62 of the inhaler body. Consequently, the user needs only to support the inhaler body 10 in a vertical position resting on the surface; the inhaler body 10, thus positioned, offers the stability needed to permit easy and rapid insertion of the capsule 2 in the relative seat 14 and a similarly easy coupling of the mouthpiece 12 to the inhaler body.

It is understood that other methods of moving the blocking tooth 52 may be envisaged.

For example, the actuation portion 64 may be flush with the rim 62 when the blocking tooth 52 is in the lowered position, and may be pushed inside the hollow portion 60 to raise the blocking tooth 52.

According to one embodiment, the blocking tooth is fitted with means of retention 66 suitable for preventing the detachment of said blocking tooth 52 from the inhaler body 10. For example, the upper portion of the blocking tooth extending above the end wall 27 of the inhaler body 10 is provided with flexible retention tabs 66 which when pressed permit the passage of said upper portion of tooth through the aperture 27' in the end wall 27, and when released, engage said end wall 27.

Advantageously, therefore, thanks to the possibility of being inserted in and extracted from the inhaler body 10 through the aperture 27 the blocking tooth 52 may be made in a single piece, for example from plastic, by moulding.

According to a further aspect of the invention, the inhaler device 1 further comprises capsule extractor means 80, suitable for penetrating the two parts 14' of capsule seat 14, so as to expel the two parts 2' of separated capsule, after the user has finished inhaling.

In one embodiment, the blocking tooth 52 has an inner cavity 52' in which said capsule extractor means 80 are housed. In particular, said capsule extractor means comprise a lower pushbutton portion 82, for example in the form of plate, housed with the possibility of axial translation in the lower actuation portion 64 of the blocking tooth. A pair of extractor teeth 84 extends vertically from said lower pushbutton portion 82, penetrating two respective seats made in the upper portion of the blocking tooth 52. The upper ends of said pair of extractor teeth project from said upper portion of the blocking tooth. The extractor teeth are axially movable between an inactive, lowered position, in which they are under the capsule seat 14, and a raised, active position, in which said ends of the extractor teeth penetrate the respective parts 14' of capsule seat through an aperture 86 made in the end wall 22 of each part of capsule seat. To such purpose, the pushbutton portion 82 of the extractor means 80 is accessible to the user through an aperture 64' made in the lower actuation portion 64 of the blocking tooth 52 to push said pushbutton portion from the inactive, lowered position to the active, raised position.

In a preferred embodiment, the extractor means 80 are fitted with elastic means 88 acting so as to normally keep said pushbutton portion 82 in a lowered, inactive position. For example, said elastic means 88 comprise a pair of leaf springs, preferably made in one piece with the pushbutton portion 82, which abut against an undercut wall 90 which delimits the lower actuation portion 64 of the blocking tooth 52 along the top.

According to a preferred embodiment, each extractor tooth 84 ends with an inclined plane 84', with decreasing incline towards the centre of the capsule seat. This way, the raising of the extractor teeth 84 also causes contemporarily the drawing together of the two parts 14' of capsule seat, and therefore the axial alignment of the extractor teeth 84 and the apertures 86 made in the end wall of the capsule seat.

In a preferred embodiment, the inhaler body 10 and the base 20 of the mouthpiece 12 are configured to axially couple to each other and are fitted with releasable snap blocking means.

Preferably, the blocking position between the inhaler body and base of the mouthpiece corresponds to the position of maximum distancing of the two parts of capsule seat.

According to one embodiment, the capsule seat 14 extends into a body chamber 92 delimited by a body side wall 94 which extends vertically from the end wall 27. For example, said body side wall 94 extends in height so as to surround, at least partially, the capsule seat 14. The base of the mouthpiece 20 is formed of a base side wall 96 which inserts with a geometric coupling into said body chamber 92 so as to surround the capsule seat 14.

In one embodiment, the separation means comprise at least one triangular shaped prominence 42 which extends from the inner side of said base side wall 96. Preferably, a pair of triangular prominences 42 extends from parallel opposite sides of the base side wall, each suitable for provoking the divarication of a pair of elastic arms 28.

In one embodiment, the snap blocking means comprise a pair of levers 98 hinged to opposite sides of the base side wall 94 and each ending with a blocking claw 100 suitable for snap-engaging a respective blocking tooth 102 made in the base side wall 96.

Preferably, said levers 98 are made in one piece with the inhaler body, for example by means of a moulding process.

At least one out of the inhaler body and the mouthpiece is provided with entrance holes 104 to permit the aspiration of a flow of air inside the inhaler device, and in particular into the body chamber 92, for mixing with the powdered substance.

In the example illustrated, such entrance holes 104 are made in an upper portion of the base side wall 96 of the mouthpiece which, when the base of the mouthpiece 20 is attached to the inhaler body, is not surrounded by the body side wall 94.

According to one embodiment, in the mouth of the exit passage 18 of the mouthpiece 12 at least one grid 110 is inserted or made having the function of ensuring that the powdered mixture contained in the capsule is correctly re-distributed in the air flow.

FIG. 8 shows an example of a grid 110 made in one piece with the mouthpiece 12, for example by means of a moulding process.

In the embodiment variation shown in FIG. 8*a*, a grid 110' is suitable for being snap-fastened to the mouthpiece. A grid seat 112 made at the mouth of the exit passage 15 of the mouthpiece and blocking teeth 114 may be noted.

In one embodiment variation shown in FIG. 8*b*, the inhaler device is fitted with a double grid 110". A different number and/or structure of the grids makes it possible to vary the resistance of the device to the air flow. The resistance of the device to the air flow is understood as the increase or decrease of differential pressure which the device creates to the passage of the air in the presence/absence of the operculum. Such resistance generated by the device may be measured in Kilo Pascal [KPa] or in any correlated unit of measure. Depending on the different conformation of the grid only, the resistance may vary, for example, taking as reference a specific resistance value of 5 kilo Pascal [Kpa], from 4 kilo Pascal at an air flow of 30 liters/minute [LPM] with a high resistance grid, to 100 LPM of air flow, when a low resistance grid is used. With grids of an intermediate conformation therefore all the intermediate flow resistance values will be possible, for example 4 KPa at a 60 LPM flow.

The value of 4 kilo Pascal [Kpa] of differential pressure is considered the benchmark value corresponding to the difference of pressure generated by a patient during the act of inhaling.

The functioning of the inhaler device according to the invention will now be described with particular reference to FIGS. 6-6e and 7-7e.

Initially the inhaler body and the mouthpiece are separate from each other. To facilitate the correct insertion of the capsule in the capsule seat, the blocking tooth is pushed into the raised position, so as to force the two parts of capsule seat against one another (FIGS. 6 and 7). For example, this is achieved by placing the inhaler body on a surface. A capsule may then be inserted in the capsule seat, for example pushing it from above in a horizontal position (FIGS. 6a and 7a).

The mouthpiece is then axially coupled to the inhaler body, leaving the blocking tooth free to move into a lowered position, and thereby permitting the parts of seat capsule to be reciprocally distanced by the separation means.

When the coupling of the inhaler body and the mouthpiece is complete, the two parts of capsule seat are completely separate, the capsule is therefore completely open and the user can proceed with the inhalation of the powdered substance (FIGS. 6b and 7b).

At the end of inhalation, the user removes the mouthpiece from the inhaler body (FIGS. 6c, 7c) and returns the blocking tooth to the raised position, so as to draw together the two parts of capsule seat, each still containing a respective part of capsule (FIGS. 6d and 7d). For example, this is achieved by placing the inhaler body on a surface.

At this point the user presses the lower pushbutton portion of the extractor means, causing the raising of the extractor teeth, their penetration in the parts of capsule seat and then the expulsion of the two parts of capsule (6e and 7e).

It is evident that the inhaler device according to the invention makes it possible to achieve the proposed objectives.

In particular, the opening of the capsule does not entail the formation of particles deriving from the rupture of its wall, as in the case of perforation or punching, which could mix with the powdered substance to be inhaled. Moreover, the complete separation of the two parts of capsule guarantees that all the powdered 15' substance is effectively released and therefore inhaled.

Advantageously, the upwardly inclined arrangement, that is towards the exit passage of the mouthpiece, of the two separate capsule parts facilitates the mixing of the powdered substance with the air flow coming from the entrance holes.

Thanks to the construction expedients described, the inhaler device is particularly reliable and safe. In case of need, the inhalation of the powdered substance may be performed extremely rapidly. For example, the insertion of the capsule in the relative seat is a fast and secure operation, in that the insertion position is univocal and intuitive.

Preferably, the inhaler device illustrated is composed of plastic material in a limited number of components (the inhaler body, the mouthpiece, the blocking tooth and extractor means), each realisable in a single piece in a plastic material by means of moulding, to the benefit of the production process and reliability of the device.

A person skilled in the art may make modifications and variations to the embodiments of the inhaler device according to the invention, replacing elements with others functionally equivalent so as to satisfy contingent requirements while remaining within the sphere of protection of the following claims. Each of the characteristics described as belonging to a possible embodiment may be realised independently of the other embodiments described.

I claim:

1. An inhaler device of a powdered substance contained in a capsule of a type having an operculum formed of two parts, comprising:
   a capsule seat suitable for receiving the capsule, said capsule seat being made in two capsule seat parts which can be reciprocally distanced, each capsule seat part being suitable to retain the respective capsule part;
   a separation means, operable to cause distancing of said two capsule seat parts and comprising at least one wedge-shaped element;
   an inhaler body wherein the capsule seat is defined;
   a mouthpiece, coupling in a detachable manner to the inhaler body, having an upper portion defining an exit passage in fluidic communication with said capsule seat and a base coupling to the inhaler body;
   said inhaler device being characterized in that the inhaler body has an end wall and a pair of elastic arms, which extend vertically from said end wall and having respective divarication surfaces parallel and facing each other, each capsule seat part being attached atop of the respective elastic arm, said at least one wedge-shaped element being suitable for inserting between said divarication surfaces to cause divarication of the pair of elastic arms.

2. The inhaler device according to claim 1, wherein each of the two capsule seat parts is suitable for blocking the capsule by interference with walls of the operculum.

3. The inhaler device according to claim 2, wherein each of the two capsule seat parts is suitable to interfere with the walls of the operculum of the capsule without causing perforation or punching of said walls.

4. The inhaler device according to claim 1, comprising a capsule seat blocker movable from an active position, in which the two capsule seat parts are blocked in a capsule insertion position, to an inactive position, in which distancing of said two capsule seat parts is permitted.

5. The inhaler device according to claim 1, comprising a capsule extractor, said capsule extractor being operable to penetrate the two capsule seat parts so as to expel the two parts of the separated capsule after a user has finished inhaling.

6. The inhaler device according to claim 1, wherein the separation means are located in said base of the mouthpiece.

7. The inhaler device according to claim 6, wherein the capsule seat is in the form of a tray orientated horizontally when the inhaler body is placed on a horizontal surface.

8. The inhaler device according to claim 1, wherein the separation means are operable to divaricate said elastic arms, so that when the divarication has been performed, the two capsule seat parts are inclined with ends facing each other upwards.

9. The inhaler device according to claim 4, wherein said capsule seat blocker comprises a blocking tooth which extends into the inhaler body under the capsule seat and which ends atop with support surfaces, each support surface suitable for engaging the respective capsule seat part, said blocking tooth being movable between a lowered position, in which said support surfaces do not interfere with the distancing movement of the two capsule seat parts, and a raised position, wherein said support surfaces press said capsule seat parts against each other.

10. The inhaler device according to claim 9, wherein each of said support surfaces is formed of an inclined plane with decreasing incline towards the capsule seat.

11. The inhaler device according to claim 9, wherein the inhaler body has a hollow lower portion which extends under said end wall and which terminates with a lower rim defining a support base of the support surfaces, and wherein the blocking tooth has a lower actuation portion which extends in said hollow lower portion passing through an aperture made in the end wall, said lower actuation portion projecting downwards from said lower rim when the blocking tooth is in the lowered position and being aligned with said rim when the blocking tooth is in the raised position.

12. The inhaler device according to claim 11, wherein an upper portion of the blocking tooth extending above the end wall is provided with flexible retention tabs which when pressed permit passage of said upper portion of the blocking tooth through the aperture in the end wall, and which engage said end wall, when in the released position, so as to prevent detachment of the blocking tooth from the inhaler body.

13. The inhaler device according to claim 5, wherein a blocking tooth has an inner cavity in which said capsule extractor are housed, and wherein said capsule extractor comprise a lower pushbutton portion, housed with the possibility of axial translation in a lower actuation portion of the blocking tooth, a pair of extractor teeth which extend vertically from said lower pushbutton portion, upper ends of the extractor teeth project from an upper portion of the blocking tooth, and elastic means acting so as to normally keep said lower pushbutton portion in a lowered, inactive position, the pushbutton portion being accessible through an aperture of the lower actuation portion of the blocking tooth to push said pushbutton portion into an active, raised position, in which said upper ends of the extractor teeth penetrate the respective capsule seat parts through an aperture made in an end wall of each capsule seat part.

14. The inhaler device according to claim 13, wherein each extractor tooth ends with an inclined plane, with decreasing incline towards a centre of the capsule seat.

15. The inhaler device according to claim 1, wherein the inhaler body and the base of the mouthpiece are configured to axially couple to each other and are fitted with releasable, snap-blocking means, a blocking position between the inhaler body and base of the mouthpiece corresponding to a position of maximum distancing of the two capsule seat parts.

16. The inhaler device according to claim 15, wherein the capsule seat extends into a body chamber delimited by a body side wall which extends vertically from the end wall, and wherein the base of the mouthpiece is formed of a base side wall which inserts with a geometric coupling into said body chamber so as to surround the capsule seat, the separation means comprising at least one triangular shaped prominence which extends from an inner side of said base side wall.

17. The inhaler device according to claim 1, wherein at least one grid inserted or made in a mouth of the exit passage of the mouthpiece is configured to permit the powdered substance contained in the capsule to re-distribute-in the air flow after opening the capsule.

* * * * *